(12) United States Patent
Field

(10) Patent No.: US 8,419,656 B2
(45) Date of Patent: *Apr. 16, 2013

(54) POST DECOMPRESSION MARKER INTRODUCER SYSTEM

(75) Inventor: Steven E Field, Grand Rapids, MI (US)

(73) Assignee: Bard Peripheral Vascular, Inc., Tempe, AZ (US)

(*) Notice: Subject to any disclaimer, the term of this patent is extended or adjusted under 35 U.S.C. 154(b) by 2152 days.

This patent is subject to a terminal disclaimer.

(21) Appl. No.: 11/535,092

(22) Filed: Sep. 26, 2006

(65) Prior Publication Data

US 2007/0038145 A1 Feb. 15, 2007

Related U.S. Application Data

(63) Continuation-in-part of application No. 10/904,666, filed on Nov. 22, 2004.

(60) Provisional application No. 60/596,467, filed on Sep. 26, 2005.

(51) Int. Cl.
*A61B 17/00* (2006.01)

(52) U.S. Cl.
USPC ............ 600/562; 606/116; 606/185; 600/431

(58) Field of Classification Search .............. 606/1, 108, 606/116, 184, 185; 600/431, 562, 564; 604/164.01, 604/264
See application file for complete search history.

(56) References Cited

U.S. PATENT DOCUMENTS

| 2,907,327 | A | 10/1959 | White |
| 3,516,412 | A | 6/1970 | Ackerman |
| 4,103,690 | A | 8/1978 | Harris |
| 4,105,030 | A | 8/1978 | Kercso |
| 4,401,124 | A | 8/1983 | Guess et al. |
| 4,405,314 | A | 9/1983 | Cope |
| 4,487,209 | A | 12/1984 | Mehl |
| 4,582,061 | A | 4/1986 | Fry |
| 4,655,226 | A | 4/1987 | Lee |
| 4,661,103 | A | 4/1987 | Harman |
| 4,682,606 | A | 7/1987 | DeCaprio |
| 4,693,237 | A | 9/1987 | Hoffman et al. |
| 4,820,267 | A | 4/1989 | Harman |
| 4,874,376 | A | 10/1989 | Hawkins, Jr. |

(Continued)

FOREIGN PATENT DOCUMENTS

| DE | 1029528 B | 5/1958 |
| EP | 0146699 A1 | 7/1985 |

(Continued)

OTHER PUBLICATIONS

Press release for Biopsys Ethicon Endo-Surgery (Europe) GmbH; The Mammotome Vacuum Biopsy System. From: http://www.medicine-news.com/articles/devices/mammotome.html. 3 pages, Jun. 6, 2000.

(Continued)

*Primary Examiner* — Kathleen Holwerda

(57) ABSTRACT

An apparatus for implanting a locatable marker at a target site within a tissue mass comprises an insertion device and a marker introducer system that is received within the insertion device. The marker introducer system is anchored in a compressed tissue mass and a locatable marker is deployed from the introducer system after the tissue mass is decompressed.

18 Claims, 19 Drawing Sheets

U.S. PATENT DOCUMENTS

| | | | |
|---|---|---|---|
| 4,909,250 A | 3/1990 | Smith | |
| 4,994,028 A | 2/1991 | Leonard et al. | |
| 5,012,818 A | 5/1991 | Joishy | |
| 5,059,197 A | 10/1991 | Urie et al. | |
| 5,125,413 A | 6/1992 | Baran | |
| 5,141,748 A | 8/1992 | Rizzo | |
| 5,162,430 A | 11/1992 | Rhee et al. | |
| 5,195,540 A | 3/1993 | Shiber | |
| 5,199,441 A | 4/1993 | Hogle | |
| 5,219,339 A | 6/1993 | Saito | |
| 5,221,269 A | 6/1993 | Miller et al. | |
| 5,242,759 A | 9/1993 | Hall | |
| 5,250,026 A | 10/1993 | Ehrlich et al. | |
| 5,273,532 A | 12/1993 | Niezink et al. | |
| 5,280,788 A | 1/1994 | Janes et al. | |
| 5,284,479 A | 2/1994 | de Jong | |
| 5,328,955 A | 7/1994 | Rhee et al. | |
| 5,353,804 A | 10/1994 | Kornberg et al. | |
| 5,354,623 A | 10/1994 | Hall | |
| 5,417,708 A | 5/1995 | Hall et al. | |
| 5,460,182 A | 10/1995 | Goodman et al. | |
| 5,475,052 A | 12/1995 | Rhee et al. | |
| 5,490,521 A | 2/1996 | Davis et al. | |
| 5,499,989 A * | 3/1996 | LaBash | 606/130 |
| 5,542,915 A | 8/1996 | Edwards et al. | |
| 5,611,352 A | 3/1997 | Kobren et al. | |
| 5,676,146 A | 10/1997 | Scarborough | |
| 5,702,716 A | 12/1997 | Dunn et al. | |
| 5,769,086 A | 6/1998 | Ritchart et al. | |
| 5,779,647 A | 7/1998 | Chau et al. | |
| 5,782,764 A | 7/1998 | Werne | |
| 5,795,308 A | 8/1998 | Russin | |
| 5,800,362 A | 9/1998 | Kobren et al. | |
| 5,800,445 A | 9/1998 | Ratcliff et al. | |
| 5,800,541 A | 9/1998 | Rhee et al. | |
| 5,821,184 A | 10/1998 | Haines et al. | |
| 5,824,042 A | 10/1998 | Lombardi et al. | |
| 5,842,999 A | 12/1998 | Pruitt et al. | |
| 5,853,366 A | 12/1998 | Dowlatshahi | |
| 5,865,806 A | 2/1999 | Howell | |
| 5,879,357 A | 3/1999 | Heaton et al. | |
| 5,897,507 A | 4/1999 | Kortenbach et al. | |
| 5,902,310 A | 5/1999 | Foerster et al. | |
| 5,911,705 A | 6/1999 | Howell | |
| 5,921,933 A | 7/1999 | Sarkis et al. | |
| 5,928,773 A | 7/1999 | Andersen | |
| 5,941,890 A | 8/1999 | Voegele et al. | |
| 5,954,670 A | 9/1999 | Baker | |
| 5,972,817 A | 10/1999 | Haines et al. | |
| 5,989,265 A | 11/1999 | Bouquet De La Joliniere et al. | |
| 6,056,700 A | 5/2000 | Burney et al. | |
| 6,066,122 A | 5/2000 | Fisher | |
| 6,096,065 A | 8/2000 | Crowley | |
| 6,096,070 A | 8/2000 | Ragheb et al. | |
| 6,106,473 A | 8/2000 | Violante et al. | |
| 6,117,108 A | 9/2000 | Woehr et al. | |
| 6,120,536 A | 9/2000 | Ding et al. | |
| 6,142,955 A | 11/2000 | Farascioni et al. | |
| 6,161,034 A | 12/2000 | Burbank et al. | |
| 6,181,960 B1 | 1/2001 | Jensen et al. | |
| 6,190,350 B1 | 2/2001 | Davis et al. | |
| 6,203,568 B1 | 3/2001 | Lombardi et al. | |
| 6,213,957 B1 | 4/2001 | Milliman et al. | |
| 6,214,045 B1 | 4/2001 | Corbitt, Jr. et al. | |
| 6,220,248 B1 * | 4/2001 | Voegele et al. | 128/898 |
| 6,228,055 B1 | 5/2001 | Foerster et al. | |
| 6,234,177 B1 | 5/2001 | Barsch | |
| 6,241,687 B1 | 6/2001 | Voegele et al. | |
| 6,261,243 B1 | 7/2001 | Burney et al. | |
| 6,261,302 B1 | 7/2001 | Voegele et al. | |
| 6,270,464 B1 | 8/2001 | Fulton, III et al. | |
| 6,270,472 B1 | 8/2001 | Antaki et al. | |
| 6,287,278 B1 | 9/2001 | Woehr et al. | |
| 6,287,332 B1 | 9/2001 | Bolz et al. | |
| 6,289,229 B1 | 9/2001 | Crowley | |
| 6,312,429 B1 | 11/2001 | Burbank et al. | |
| 6,335,029 B1 | 1/2002 | Kamath et al. | |
| 6,336,904 B1 | 1/2002 | Nikolchev | |
| 6,340,367 B1 | 1/2002 | Stinson et al. | |
| 6,343,227 B1 | 1/2002 | Crowley | |
| 6,347,241 B2 | 2/2002 | Burbank et al. | |
| 6,350,244 B1 | 2/2002 | Fisher | |
| 6,356,782 B1 | 3/2002 | Sirimanne et al. | |
| 6,358,217 B1 | 3/2002 | Bourassa | |
| 6,371,904 B1 | 4/2002 | Sirimanne et al. | |
| 6,405,733 B1 | 6/2002 | Fogarty et al. | |
| 6,409,742 B1 | 6/2002 | Fulton, III et al. | |
| 6,425,903 B1 | 7/2002 | Voegele | |
| 6,427,081 B1 | 7/2002 | Burbank et al. | |
| 6,471,700 B1 | 10/2002 | Burbank et al. | |
| 6,506,156 B1 | 1/2003 | Jones et al. | |
| 6,551,253 B2 | 4/2003 | Worm et al. | |
| 6,564,806 B1 | 5/2003 | Fogarty et al. | |
| 6,567,689 B2 | 5/2003 | Burbank et al. | |
| 6,575,991 B1 | 6/2003 | Chesbrough et al. | |
| 6,605,047 B2 | 8/2003 | Zarins et al. | |
| 6,616,630 B1 | 9/2003 | Woehr et al. | |
| 6,626,850 B1 | 9/2003 | Chau et al. | |
| 6,636,758 B2 | 10/2003 | Sanchez et al. | |
| 6,638,234 B2 | 10/2003 | Burbank et al. | |
| 6,656,192 B2 | 12/2003 | Espositio et al. | |
| 6,662,041 B2 | 12/2003 | Burbank et al. | |
| 6,712,774 B2 | 3/2004 | Voegele et al. | |
| 6,716,444 B1 | 4/2004 | Castro et al. | |
| 6,725,083 B1 * | 4/2004 | De Santis et al. | 600/431 |
| 6,730,044 B2 | 5/2004 | Stephens et al. | |
| 6,746,773 B2 | 6/2004 | Llanos et al. | |
| 6,752,154 B2 | 6/2004 | Fogarty et al. | |
| 6,766,186 B1 | 7/2004 | Hoyns et al. | |
| 6,774,278 B1 | 8/2004 | Ragheb et al. | |
| 6,780,179 B2 * | 8/2004 | Lee et al. | 606/34 |
| 6,824,527 B2 | 11/2004 | Gollobin | |
| 6,846,320 B2 * | 1/2005 | Ashby et al. | 606/213 |
| 6,862,470 B2 | 3/2005 | Burbank et al. | |
| 6,863,685 B2 | 3/2005 | Davila et al. | |
| 6,899,731 B2 | 5/2005 | Li et al. | |
| 6,918,927 B2 | 7/2005 | Bates et al. | |
| 6,936,014 B2 * | 8/2005 | Vetter et al. | 600/564 |
| 6,951,564 B2 | 10/2005 | Espositio et al. | |
| 6,993,375 B2 | 1/2006 | Burbank et al. | |
| 6,994,712 B1 | 2/2006 | Fisher et al. | |
| 6,996,433 B2 | 2/2006 | Burbank et al. | |
| 7,001,341 B2 | 2/2006 | Gellman et al. | |
| 7,008,382 B2 | 3/2006 | Adams et al. | |
| 7,014,610 B2 | 3/2006 | Koulik | |
| 7,025,765 B2 | 4/2006 | Balbierz et al. | |
| 7,044,957 B2 | 5/2006 | Foerster et al. | |
| 7,047,063 B2 | 5/2006 | Burbank et al. | |
| 7,083,576 B2 | 8/2006 | Zarins et al. | |
| 7,125,397 B2 | 10/2006 | Woehr et al. | |
| 7,214,211 B2 | 5/2007 | Woehr et al. | |
| 7,229,417 B2 | 6/2007 | Foerster et al. | |
| 7,236,816 B2 | 6/2007 | Kumar et al. | |
| 7,264,613 B2 | 9/2007 | Woehr et al. | |
| 7,294,118 B2 | 11/2007 | Saulenas et al. | |
| 7,416,533 B2 | 8/2008 | Gellman et al. | |
| 7,424,320 B2 | 9/2008 | Chesbrough et al. | |
| 7,449,000 B2 | 11/2008 | Adams et al. | |
| 7,527,610 B2 | 5/2009 | Erickson | |
| 7,569,065 B2 | 8/2009 | Chesbrough et al. | |
| 7,577,473 B2 | 8/2009 | Davis et al. | |
| 7,670,350 B2 * | 3/2010 | Selis | 606/151 |
| 2002/0004060 A1 | 1/2002 | Heublein et al. | |
| 2002/0016612 A1 * | 2/2002 | Ashby et al. | 606/213 |
| 2002/0016625 A1 | 2/2002 | Falotico et al. | |
| 2002/0026201 A1 | 2/2002 | Foerster et al. | |
| 2002/0035324 A1 | 3/2002 | Sirimanne et al. | |
| 2002/0045842 A1 | 4/2002 | Van Bladel et al. | |
| 2002/0058868 A1 | 5/2002 | Hoshino et al. | |
| 2002/0077687 A1 | 6/2002 | Ahn | |
| 2002/0082519 A1 | 6/2002 | Miller et al. | |
| 2002/0082682 A1 | 6/2002 | Barclay et al. | |
| 2002/0095204 A1 | 7/2002 | Thompson et al. | |
| 2002/0107437 A1 | 8/2002 | Sirimanne et al. | |
| 2002/0143359 A1 | 10/2002 | Fulton, III et al. | |
| 2002/0165608 A1 | 11/2002 | Llanos et al. | |
| 2002/0193815 A1 | 12/2002 | Foerster et al. | |

| | | |
|---|---|---|
| 2002/0193867 A1 | 12/2002 | Gladdish, Jr. et al. |
| 2003/0225420 A1 | 12/2003 | Wardle |
| 2003/0233101 A1 | 12/2003 | Lubock et al. |
| 2004/0016195 A1 | 1/2004 | Archuleta |
| 2004/0024304 A1 | 2/2004 | Foerster et al. |
| 2004/0073107 A1 | 4/2004 | Sioshansi et al. |
| 2004/0073284 A1 | 4/2004 | Bates et al. |
| 2004/0077971 A1 * | 4/2004 | Vetter et al. .................. 600/564 |
| 2004/0097981 A1 * | 5/2004 | Selis ........................ 606/151 |
| 2004/0106891 A1 | 6/2004 | Langan et al. |
| 2004/0116802 A1 | 6/2004 | Jessop et al. |
| 2004/0124105 A1 | 7/2004 | Seiler et al. |
| 2004/0127765 A1 | 7/2004 | Seiler et al. |
| 2004/0162574 A1 | 8/2004 | Viola |
| 2004/0210208 A1 | 10/2004 | Paul et al. |
| 2004/0236212 A1 | 11/2004 | Jones et al. |
| 2005/0020916 A1 | 1/2005 | MacFarlane et al. |
| 2005/0033157 A1 | 2/2005 | Klein et al. |
| 2005/0033195 A1 | 2/2005 | Fulton et al. |
| 2005/0036946 A1 | 2/2005 | Pathak et al. |
| 2005/0080339 A1 | 4/2005 | Sirimanne et al. |
| 2005/0100580 A1 | 5/2005 | Osborne et al. |
| 2005/0113659 A1 | 5/2005 | Pothier et al. |
| 2005/0119562 A1 | 6/2005 | Jones et al. |
| 2005/0143650 A1 | 6/2005 | Winkel |
| 2005/0165305 A1 | 7/2005 | Foerster et al. |
| 2005/0234336 A1 | 10/2005 | Beckman et al. |
| 2005/0273002 A1 | 12/2005 | Goosen et al. |
| 2005/0277871 A1 | 12/2005 | Selis |
| 2006/0025795 A1 | 2/2006 | Chesbrough et al. |
| 2006/0036158 A1 | 2/2006 | Field et al. |
| 2006/0036165 A1 | 2/2006 | Burbank et al. |
| 2006/0074443 A1 | 4/2006 | Foerster et al. |
| 2006/0079805 A1 | 4/2006 | Miller et al. |
| 2006/0116573 A1 | 6/2006 | Field et al. |
| 2006/0173280 A1 | 8/2006 | Goosen et al. |
| 2006/0173296 A1 | 8/2006 | Miller et al. |
| 2006/0177379 A1 | 8/2006 | Asgari |
| 2006/0217635 A1 | 9/2006 | McCombs et al. |
| 2006/0235298 A1 | 10/2006 | Kotmel et al. |
| 2006/0241411 A1 | 10/2006 | Field et al. |
| 2007/0083132 A1 | 4/2007 | Sharrow |
| 2007/0087026 A1 | 4/2007 | Field |
| 2007/0135711 A1 | 6/2007 | Chernomorsky et al. |
| 2007/0142725 A1 | 6/2007 | Hardin et al. |
| 2007/0239118 A1 | 10/2007 | Ono et al. |
| 2007/0287933 A1 | 12/2007 | Phan et al. |
| 2008/0033280 A1 | 2/2008 | Lubock et al. |
| 2008/0097199 A1 | 4/2008 | Mullen |
| 2008/0188768 A1 | 8/2008 | Zarins et al. |
| 2008/0269638 A1 | 10/2008 | Cooke et al. |
| 2009/0069713 A1 | 3/2009 | Adams et al. |
| 2009/0093714 A1 | 4/2009 | Chesbrough et al. |
| 2009/0131825 A1 | 5/2009 | Burbank et al. |
| 2010/0010341 A1 | 1/2010 | Talpade et al. |
| 2010/0030072 A1 | 2/2010 | Casanova et al. |
| 2010/0030149 A1 | 2/2010 | Carr, Jr. |

FOREIGN PATENT DOCUMENTS

| | | |
|---|---|---|
| EP | 0769281 A2 | 4/1997 |
| EP | 1163888 A1 | 12/2001 |
| EP | 1364628 A1 | 11/2003 |
| FR | 2646674 A3 | 11/1990 |
| WO | 9806346 A1 | 2/1998 |
| WO | 9908607 A1 | 2/1999 |
| WO | 0023124 A1 | 4/2000 |
| WO | 0024332 A1 | 5/2000 |
| WO | 0028554 A1 | 5/2000 |
| WO | 0108578 A1 | 2/2001 |
| WO | 0170114 A1 | 9/2001 |
| WO | 03000308 A1 | 1/2003 |
| WO | 2004045444 A2 | 6/2004 |
| WO | 2006097331 A2 | 9/2006 |

OTHER PUBLICATIONS

Johnson & Johnson: Breast Biopsy (minimally invasive): Surgical Technique: Steps in the MAMOTOME Surgical Procedure. From http://www.jnjgateway.com. 3 pages, Jun. 6, 2000.

Johnson & Johnson: New Minimally Invasive Breast Biopsy Device Receives Marketing Clearance in Canada; Aug. 6, 1999. From http://www.jnjgateway.com. 4 pages.

Johnson & Johnson: MAMMOTOME Hand Held Receives FDA Marketing Clearance for Minimally Invasive Breast Biopises; Sep. 1, 1999. From From http://www.jnjgateway.com. 5 pages.

Johnson & Johnson: The Mammotome Breast Biopsy System. From: http://www.breastcareinfo.com/aboutm.htm. 6 pages, Jun. 6, 2000.

Cook Incorporated: Emoblization and Occlusion. From: www.cookgroup.com 6 pages, 1997.

Liberman, Laura, et al. Percutaneous Removal of Malignant Mammographic Lesions at Stereotactic Vacuum-assisted Biopsy. From: The Departments of Radiology, Pathology, and Surgery. Memorial Sloan-Kettering Cancer Center. From the 1997 RSNA scientific assembly. vol. 206, No. 3. pp. 711-715.

* cited by examiner

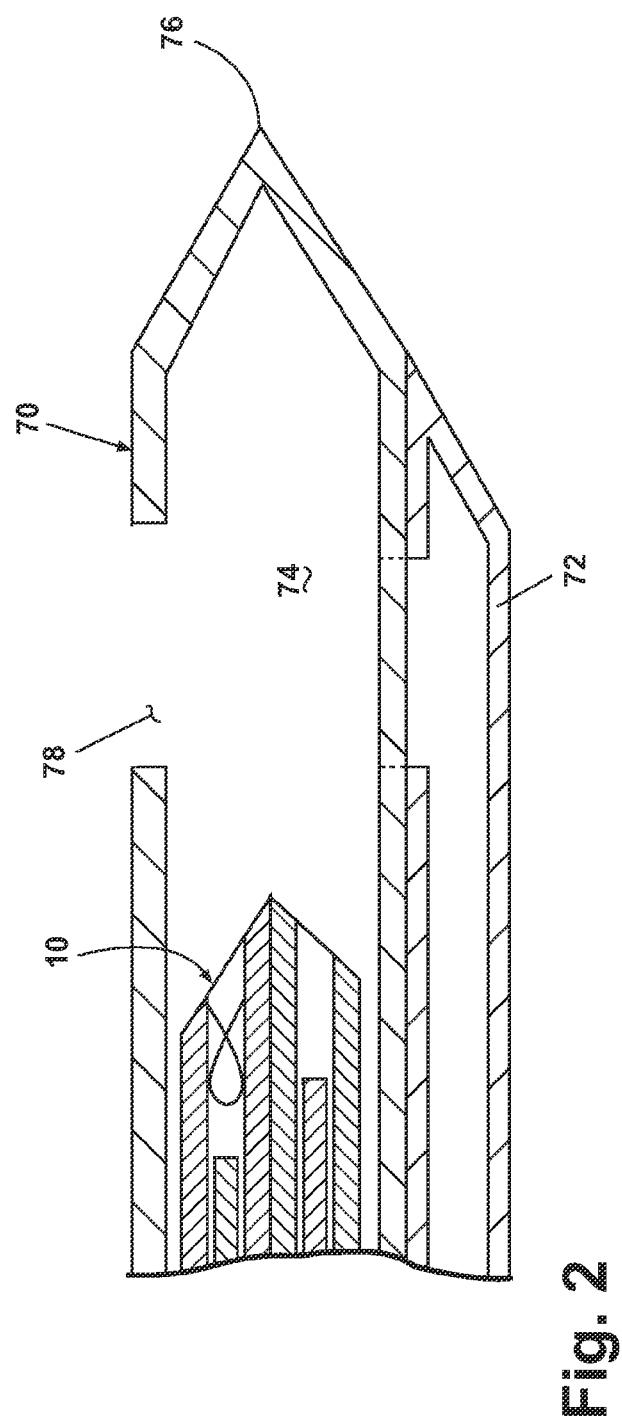
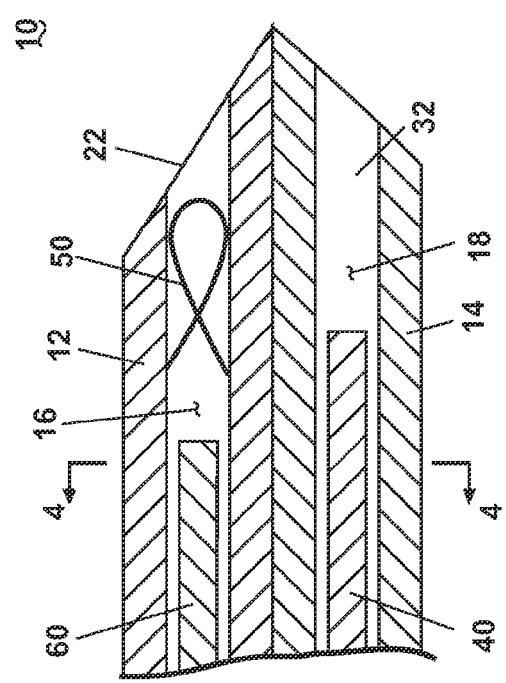
Fig. 2
Fig. 3

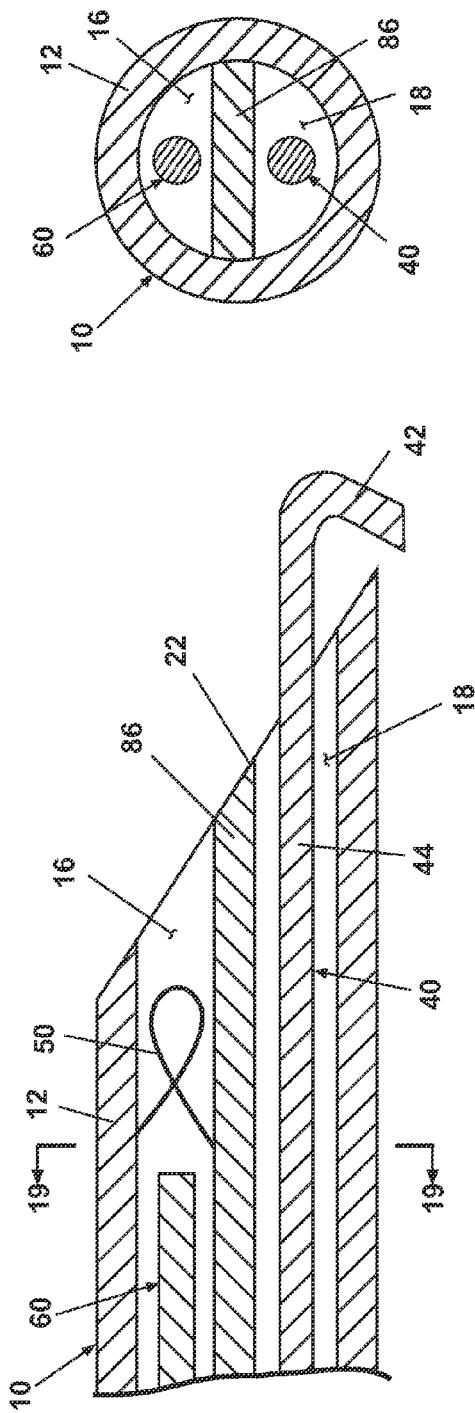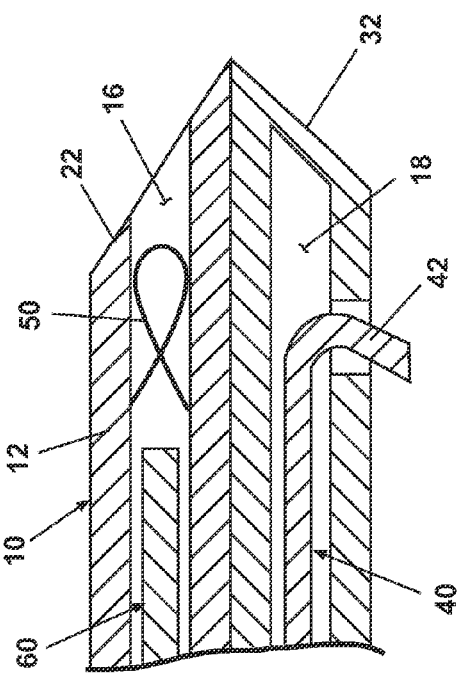

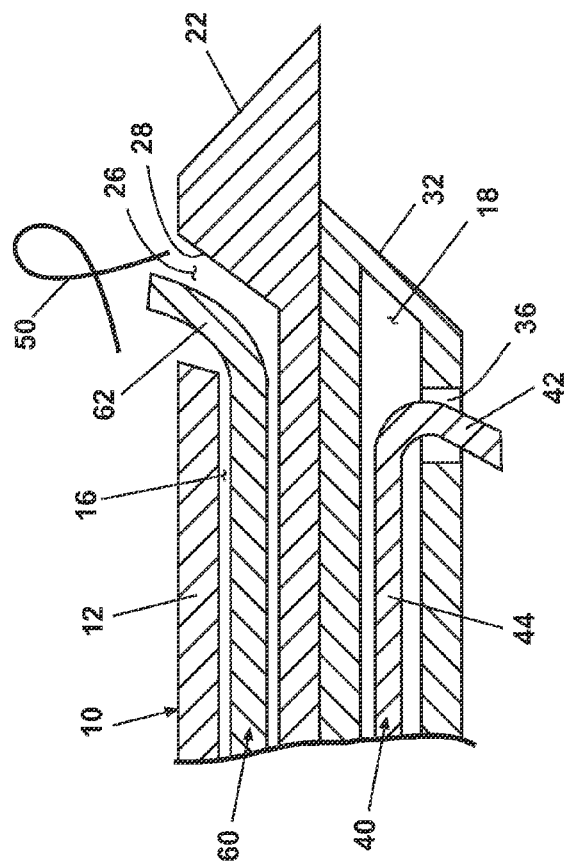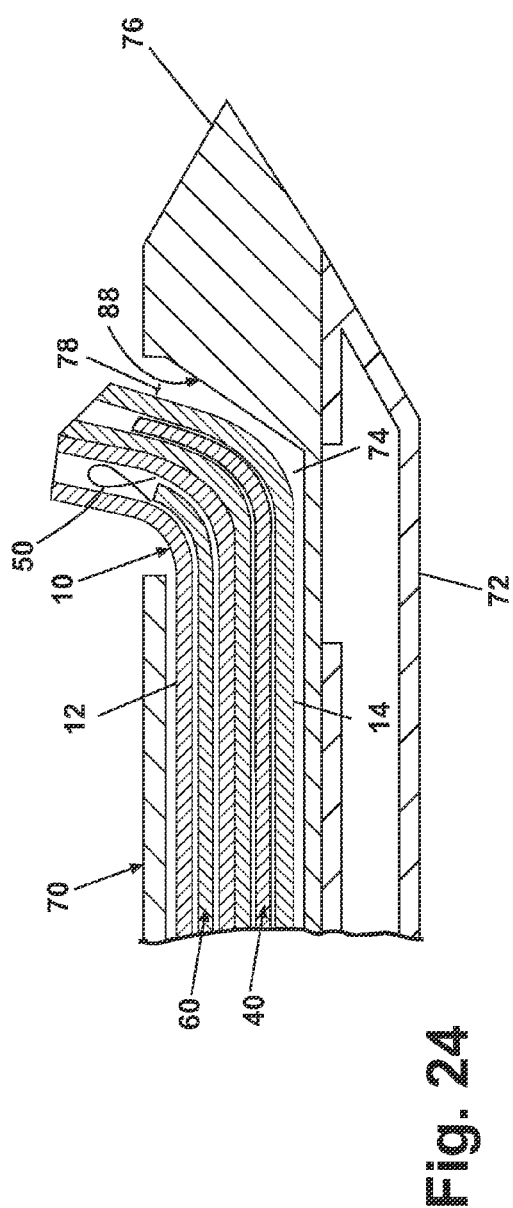

POST DECOMPRESSION MARKER INTRODUCER SYSTEM

CROSS-REFERENCE TO RELATED APPLICATIONS

This application is a continuation-in-part of U.S. patent application Ser. No. 10/904,666, filed Nov. 22, 2004, and further claims the benefit of U.S. Provisional Patent Application No. 60/596,467, filed Sep. 26, 2005, both of which are incorporated herein by reference in its entirety.

BACKGROUND OF THE INVENTION

1. Field of the Invention

This invention relates generally to a medical device for marking a target site within a tissue mass and more specifically to a medical device having a marker for marking a biopsy site in breast tissue that is deployed after the breast tissue has been decompressed.

2. Description of the Related Art

A biopsy is a well-known medical procedure that involves taking a sample of tissue from a person and examining it for diagnostic purposes. This is often done when an abnormality is found in a tissue mass, for example when a lump is found in breast tissue or when an imaging system, such as mammography or ultrasonography detects a suspicious area. Examining a sample of tissue from an abnormal site or lesion is currently the only way to accurately diagnose cancer.

A vacuum-assisted biopsy (VAB) uses an imaging system, such as ultrasonography or mammography, to locate a lesion in the breast tissue and to guide a biopsy probe to the site. An example of a known VAB device 200 is shown in FIG. 1. Such a VAB device is described in U.S. Pat. No. 6,712,774 and is incorporated by reference in its entirety. The details of the VAB device are not germane to the invention and thus will only be briefly described. The probe 70 has a pointed tip 76 to facilitate its insertion through the tissue mass, an opening 78 in the side wall of the probe near the pointed tip, and a vacuum chamber 72. Once the probe 70 is in position at the lesion site, a vacuum pump creates a vacuum in chamber 72 and draws the tissue through the opening 78 and into a sampling chamber where a cutting device is advanced through the probe 70 to cut and remove a tissue sample. Other instruments can be inserted through the probe 70 in addition to the cutting device.

The position of the patient during VAB depends on the imaging system used to locate the lesion and position the probe. If ultrasonography is used, the patient will be in a supine position. If mammography is used, the patient typically lies prone on a specialized table such that the breast protrudes through a hole in the table. The breast is compressed between two plates while an image of the lesion is produced on a monitor by a mammography unit. Once the lesion is imaged, the VAB probe, which is mounted to the table or the mammography unit, is inserted into the breast tissue and the tissue sample is gathered as described above.

In some cases, it is desirable to mark the location of the lesion site in case a future biopsy or surgery is necessary. This is done with a marker that is made of any suitable material that can be imaged by an imaging system, such as ultrasonography, magnetic resonance, or mammography, or that is palpable through the skin and tissue of the patient. The marker must be accurately placed at the lesion site in the breast tissue and must remain at the site so that the lesion can be located and identified at a later time, if necessary. However, there sometimes is a need for a marker to be repositioned after its initial placement, such as if the marker was not placed at the desired location or if the marker shifts upon decompression of the tissue. Thus, the marker must be able to remain anchored in the breast tissue, yet permit its repositioning.

One type of marker is a biocompatible clip that can be placed at the lesion site to facilitate locating the lesion during later procedures. The clip has the advantage of being implanted entirely within the tissue mass, so that there is no possibility of accidental repositioning by pulling or tugging the clip. The clip is placed after the tissue sample has been gathered from the lesion site and while the breast is still compressed. The clip is inserted into the tissue mass through the VAB probe and thus does not require the tissue mass to be repierced. Since the clip is deployed when the breast tissue is compressed, upon decompression the clip may be found to be implanted away from the lesion site, leading to inaccurate marking of the lesion site. An illustrative example of the post-decompression shifting problem is a rubber ball that is normally 5 cm in diameter, but compressed to 2 cm. If a clip is to be placed 1 cm from the edge of the ball, the clip would be placed at the center of the ball. However, if upon decompression of the ball the clip stays at the center of the ball or shifts away from the target site, the clip is misplaced by up to several centimeters. Coopers ligaments in the breast exacerbate the problem of inaccurate marking by acting to pull the clip away from the site of implantation when the breast is uncompressed.

SUMMARY OF THE INVENTION

According to one aspect of the present invention, a method for implanting a locatable marker in a tissue mass, comprises compressing the tissue mass, locating a target site within the tissue mass, inserting the locatable marker into the tissue mass at the target site, decompressing the tissue mass, and repositioning the locatable marker to the target site if the locatable marker is not at the target site after decompressing the tissue mass.

The inserting step can comprise inserting a sheath containing the locatable marker into the tissue mass at the target site. The inserting step can further comprise anchoring the sheath containing the locatable marker at the target site. Anchoring the sheath can comprise embedding an anchor wire in the tissue mass.

The repositioning step can comprise locating the locatable marker and the target site using an imaging system to determine the position of the locatable marker relative to the target site. The repositioning step can further comprise implanting the locatable marker at the tissue site after the locatable marker is determined to be at the target site. The repositioning step can further comprise relocating the locatable marker to the target site before implanting the locatable marker.

The repositioning step can further comprise locating the sheath and the target site using an imaging system to determine the position of the sheath relative to the target site. The repositioning step can further comprise implanting the locatable marker at the tissue site after the locatable marker is determined to be at the target site. The repositioning step can further comprise one of advancing and retracting the sheath to the target site before implanting the locatable marker.

The method can further comprise inserting an insertion device into the compressed tissue mass prior to inserting the locatable marker. The inserting step can further comprise inserting a sheath containing the locatable marker through the insertion device. The method can further comprise withdrawing the insertion device from the tissue mass prior to the repositioning step.

The target site can be one of a lesion site and a biopsy site.

According to another aspect of the invention, a method for implanting a locatable marker in a tissue mass comprises compressing the tissue mass, locating a target site within the tissue mass, anchoring a sheath containing the locatable marker at the target site, decompressing the tissue mass, and deploying the locatable marker at the target site after decompressing the tissue mass.

The anchoring step can comprise inserting the sheath containing the locatable marker and an anchor wire into the tissue mass at the target site. The anchoring step can further comprise embedding the anchor wire at the target site. Embedding the anchor wire can comprise extending the anchor wire from within a lumen of the sheath to the target site.

The deploying step can comprise implanting the locatable marker at the tissue site after decompressing the tissue mass. Implanting the locatable marker can comprise pushing the locatable marker from a lumen of the sheath using a pushrod. The deploying step can further comprise deploying a hemostatic agent with the locatable marker. The deploying step can further comprise locating the sheath and the target site using a locatable system before implanting the locatable marker to determine the position of the locatable marker relative to the tissue site. The deploying step can further comprise relocating the locatable marker to the target site before implanting the locatable marker. Relocating the locatable marker can comprise retracting the sheath a predetermined distance to the target site. Relocating the locatable marker can comprise inserting a cannula over the sheath and advancing the cannula, with the sheath contained therein, a predetermined distance to the target site.

The method can further comprise inserting an insertion device into the compressed tissue mass prior to the anchoring step. The anchoring step can further comprise inserting a sheath containing the locatable marker through the insertion device. The method can further comprise withdrawing the insertion device from the tissue mass prior to the deploying step.

The target site can be one of a lesion site and a biopsy site.

According to yet another aspect of the invention, an apparatus for implanting a locatable marker at a target site within a tissue mass comprises an insertion device comprising a first lumen having an exit opening, a sheath slidably received within the first lumen and comprising a second lumen having a distal opening, a locatable marker received within the second lumen and deployable through the distal opening, and an anchor operably coupled to the sheath to fix the location of the sheath in the tissue mass, wherein the insertion device can be located within the tissue mass and the sheath can be inserted into the tissue mass through the exit opening of the insertion device, and the anchor can fix the position of the sheath in the tissue mass for deployment of the locatable marker at the target site.

The insertion device can be a biopsy probe. The probe can be a vacuum-assisted biopsy probe. The exit opening can comprise a ramp.

The sheath can comprise a third lumen having a distal opening, with the anchor received within the third lumen and deployable through the distal opening. The sheath can comprise a distal terminal end and the distal terminal end can comprise an insertion tip. At least one of the sheath distal openings can be formed in the distal terminal end of the sheath. At least one of the sheath distal openings can be formed in a side wall of the sheath. At least one of the sheath distal openings formed in the side wall can comprise a ramp to guide the locatable marker through at least one of the sheath distal openings formed in the side wall.

The sheath can be flexible. The sheath can comprise distance markings.

The apparatus can further comprise a pushrod slidably received within the second lumen that deploys the locatable marker through the distal opening.

The locatable marker can be one of an imaging marker and a palpable marker. The locatable marker can be a clip.

The anchor can comprise an anchor wire. The sheath can comprise a third lumen having a distal opening and the anchor wire can be received within the third lumen. The anchor wire can be operable between a straight configuration where the anchor wire is contained within the third lumen and a curved configuration where the anchor wire is extended through the distal opening of the third lumen. The anchor wire can be embedded in the tissue mass in the curved configuration.

The apparatus can further comprise a cannula received within the first lumen, the cannula comprising a fourth lumen having a distal opening, with the sheath received within the fourth lumen. The cannula distal opening can comprise a ramp to guide the sheath through the cannula distal opening.

The apparatus can further comprising a pair of compression plates for compressing the tissue mass prior to location of the insertion device into the tissue mass at the target site and for decompressing the tissue mass prior to implantation of the locatable marker.

The apparatus can further comprise a hemostatic agent received within the second lumen and deployable through the distal opening

BRIEF DESCRIPTION OF THE DRAWINGS

In the drawings:

FIG. 2 is a schematic illustration of a VAB probe containing an introducer system according to the first embodiment of the present invention comprising a sheath having a first lumen containing a marker clip and a pushrod and a second lumen containing an anchor wire.

FIG. 3 is an enlarged view of the first embodiment of the introducer system from FIG. 2.

FIG. 18 is an enlarged view of a second embodiment of the introducer system.

FIG. 19 is a sectional view of the introducer system taken along line 19-19 from FIG. 18.

FIG. 20 is an enlarged view of a third embodiment of the introducer system showing the anchor wire extended from the second lumen.

FIG. 23 is an enlarged view of a fourth embodiment of the introducer system.

FIG. 24 is an enlarged view of a second embodiment of the VAB probe.

DESCRIPTION OF THE PREFERRED EMBODIMENT

Figure 1:
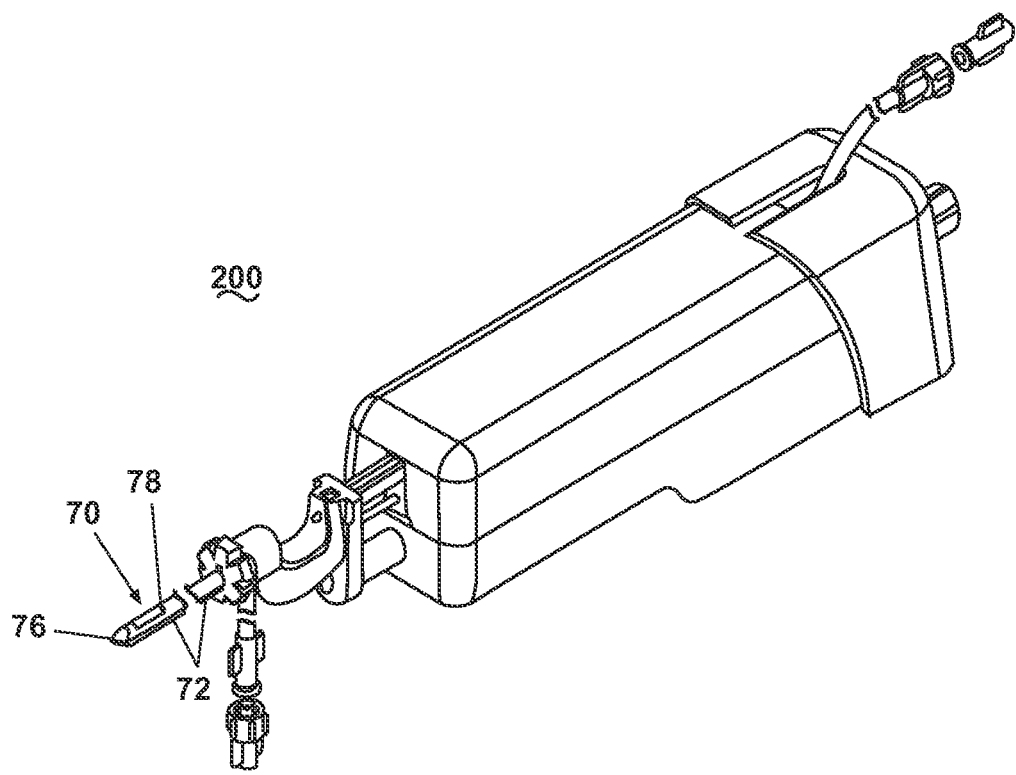
FIG. 1 is a schematic illustration of a prior art VAB device.

Referring now to the drawings and particularly to FIG. 2, an embodiment of the marker introducer system 10 is illustrated contained within a VAB probe 70 of a VAB system (FIG. 1). The VAB probe 70 comprises a vacuum chamber 72, a lumen 74, a closed insertion tip 76, and a proximal opening (not shown) into which the introducer system 10 can be inserted. An opening 78 in the cannula 72 allows a tissue sample to be taken from a tissue mass as previously described.

Referring additionally to FIG. 3, the introducer system 10 comprises a first sheath 12 and a second sheath 14 which respectively define a first lumen 16 and a second lumen 18. The first sheath 12 comprises an open distal insertion tip 22 and an open proximal end (not shown). The second sheath 14 comprises an open distal tip 32 and an open proximal end (not shown). An anchor wire 40 is contained within the second lumen 18 and a marker in the form of a clip 50 and a pushrod 60 are contained within the first lumen 16.

Figure 4:
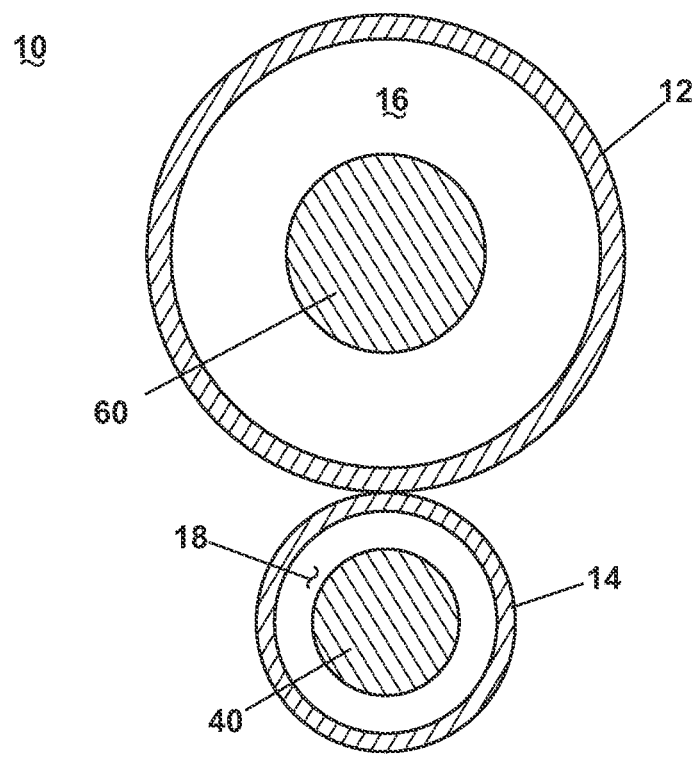
FIG. 4 is a sectional view of the introducer system taken along line 4-4 from FIG. 3.

The sheaths 12, 14 are preferably independently fabricated from a biocompatible plastic that is flexible and bonded together as shown in FIG. 4. The gap between the sheaths 12, 14 and the corresponding pushrod 60 and anchor wire 40 is exaggerated in FIG. 3 to better discern the elements. One or both of the sheaths 12, 14 could also be formed from a coiled wire or any other biocompatible material that is sufficiently flexible such that the introducer system 10 can be inserted through the VAB probe and out of the opening 78.

Figure 5:
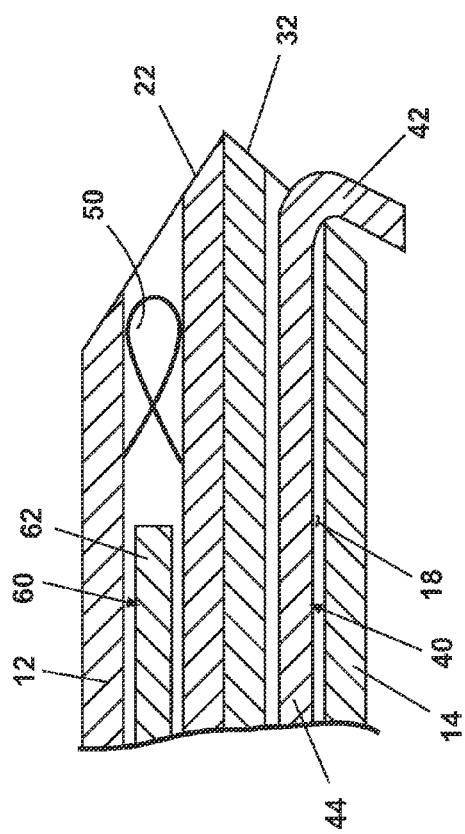
FIG. 5 is a drawing similar to FIG. 3 illustrating the anchor wire extended from the second lumen.

Referring to FIG. 5, the anchor wire 40 comprises a hook 42 and a thread 44. When mounted in the sheath 14 prior to implantation in the tissue mass, the hook 42 is contained within the second lumen 18 and a portion of the thread 44 extends exteriorly from the proximal end of the sheath 14. The thread 44 is of sufficient length such that the proximal end of the thread 44 is exterior to the proximal end of the sheath 14 to manipulate the anchor wire 40 relative to the sheath 14.

The hook 42 is fabricated from a resilient, biocompatible material, for example a shape-memory alloy such as Nitinol. This allows the hook to assume a straight first configuration in the lumen as illustrated in FIG. 3, and a curved second configuration outside the lumen as illustrated in FIG. 5.

The hook 42 is preferably formed from the same wire as the thread 44 such that the hook is a continuation of the thread with the end of the hook 42 being connected to the thread 42 to complete hook 42. Alternately, the hook 42 and the thread 44 can be formed from different wires and or different materials. In either case, the hook 42 can be bonded or welded to the thread 44 to form the connection.

While the anchor wire 40 is shown having a hook 42 that engages the tissue mass, the anchor wire 40 can be formed with any one of a number of different anchors. For instance, as disclosed in U.S. patent application Ser. No. 10/904,666, the anchor wire 40 can be formed with a diamond or square shaped anchor, a triangular shaped anchor, a circular shaped anchor, or any other anchor shape or type that provides a secure implantation of the introducer system 10 in the tissue mass. The shape of the anchor can be selected upon, for example, the density of the tissue into which the wire is to be placed, the size of the lesion, and/or the anchoring force required to implant the introducer system 10 in the tissue mass.

While only one anchor wire 40 is illustrated in the embodiments shown herein, it is understood that the introducer system 10 can comprise more than one anchoring device. For example, the introducer system 10 can have multiple anchor wires 40 loaded in the second sheath 14, or the introducer system 10 can have multiple sheaths that each hold one anchor wire 40. In either case, the anchor wires 40 can be configured to engage the tissue mass at different angles to provide for a more secure implantation of the introducer system 10.

Figure 6:
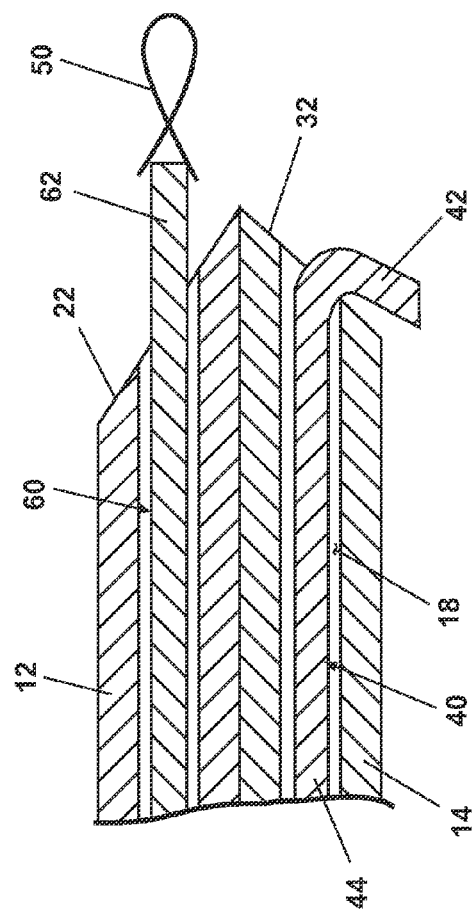
FIG. 6 is a drawing similar to FIG. 5 illustrating the pushrod extended from the first lumen to push the marker clip out of the introducer system.
Figure 7:
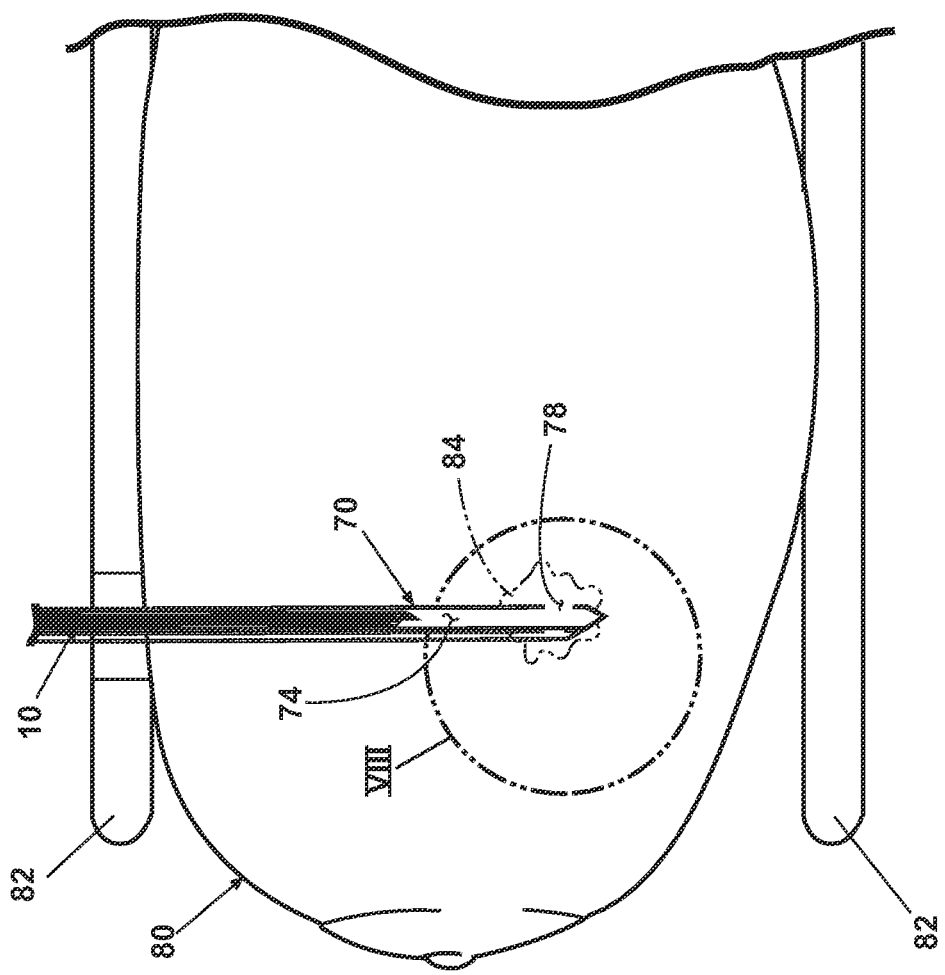
FIG. 7 is a schematic illustration of the VAB probe from FIG. 2 inserted into a tissue mass comprising a breast that is compressed between compression plates.

Referring to FIG. 6, the pushrod 60 comprises a distal end 62 and a proximal end (not shown). The distal end 62 is used to force the clip 50 out of the sheath 12 and into the tissue mass. The pushrod 60 is of sufficient length such that the proximal end of the pushrod is exterior to the proximal end of the sheath 12 to manipulate the pushrod 60 relative to the sheath 12. The pushrod 60 can be made of any material that is sufficiently flexible in order to be threaded through the sheath 12, yet stiff enough to push the clip 50 out of the open tip 22 of the sheath 12.

The clip 50 can be any suitable type of marker that can be detected and located. The clip 50 can be imaged by an imaging technique or palpable through the skin and tissue. Types of imagable markers include markers that are echogenic, radiopaque, or a combination of these types. The imaging technique used locate the clip 50 can be a standard imaging system such as ultrasonography, mammography or magnetic resonance imaging.

Figure 8:
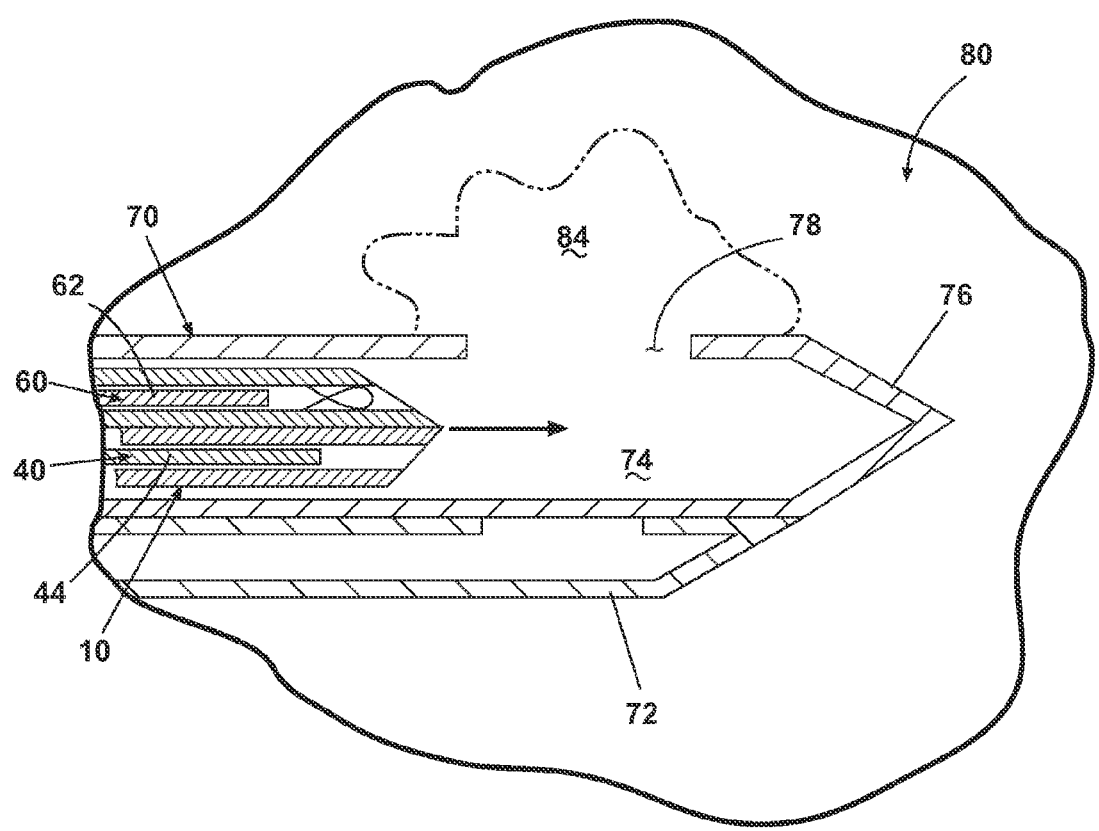
FIG. 8 is a close-up view of area VIII from FIG. 7 illustrating the insertion of the introducer system into the VAB probe.
Figure 9:
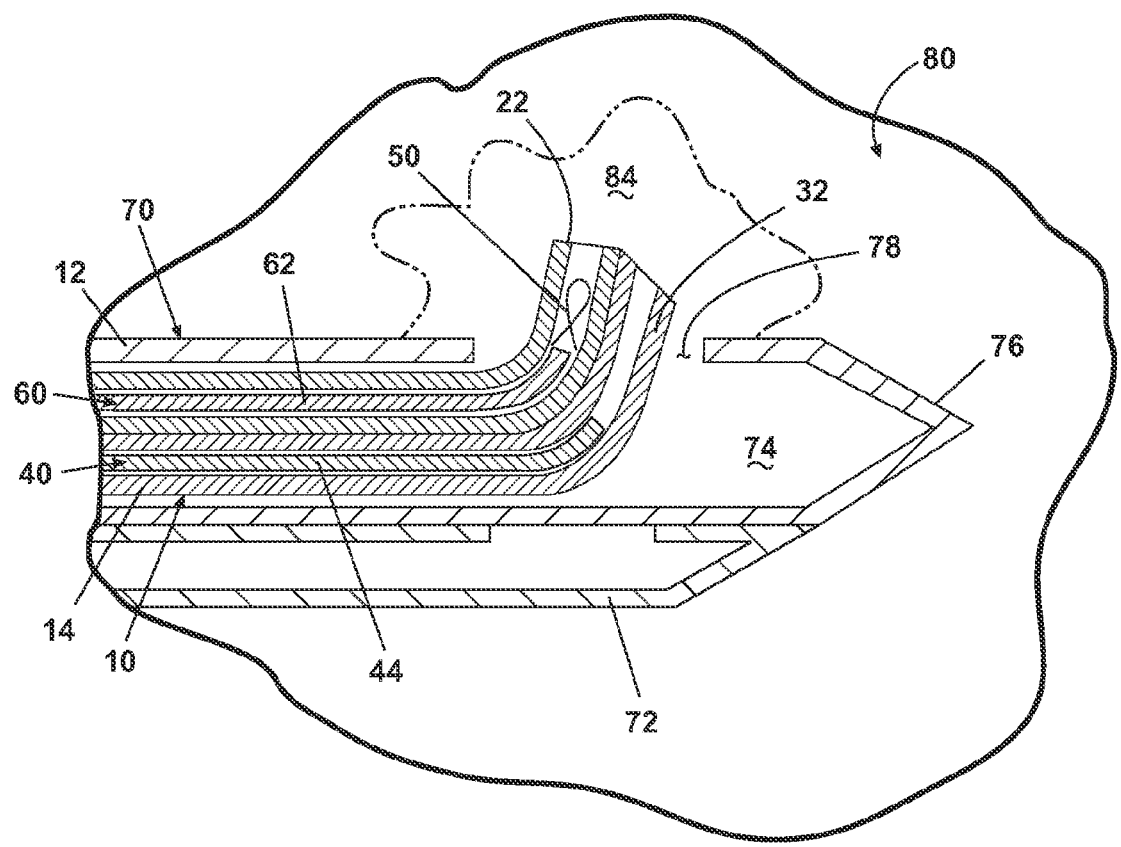
FIG. 9 is a drawing similar to FIG. 8 illustrating the introducer system extended from the VAB probe and into the tissue mass.

Referring to FIGS. 7-13, the clip 50 is deployed into the tissue mass as follows. The VAB probe 70 is inserted into the tissue mass 80 illustrated as a breast that is compressed between two plates 82 and containing a target site 84. The target site can comprise a lesion or biopsy site. Referring to FIG. 8, after a VAB procedure has been performed during which a sample of tissue is taken from the target site 84, the introducer system 10 is inserted through the open proximal end of the VAB probe 70. Referring to FIG. 9, the introducer system is threaded through lumen 74 and through opening 78 so that the distal tips 22, 32 of the sheaths 12, 14 protrude into the tissue mass 80.

Figure 10:
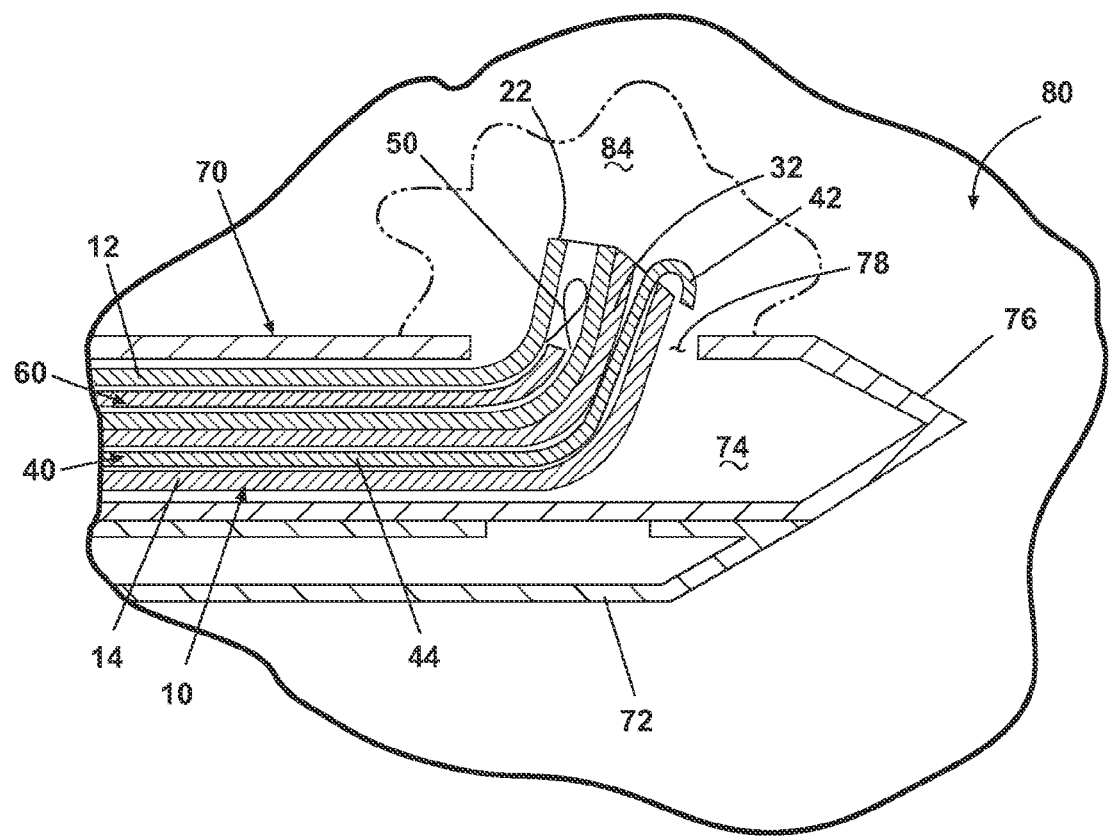
FIG. 10 is a drawing similar to FIG. 9 illustrating the anchor wire extended from the second lumen and anchored in the tissue mass.
Figure 11:
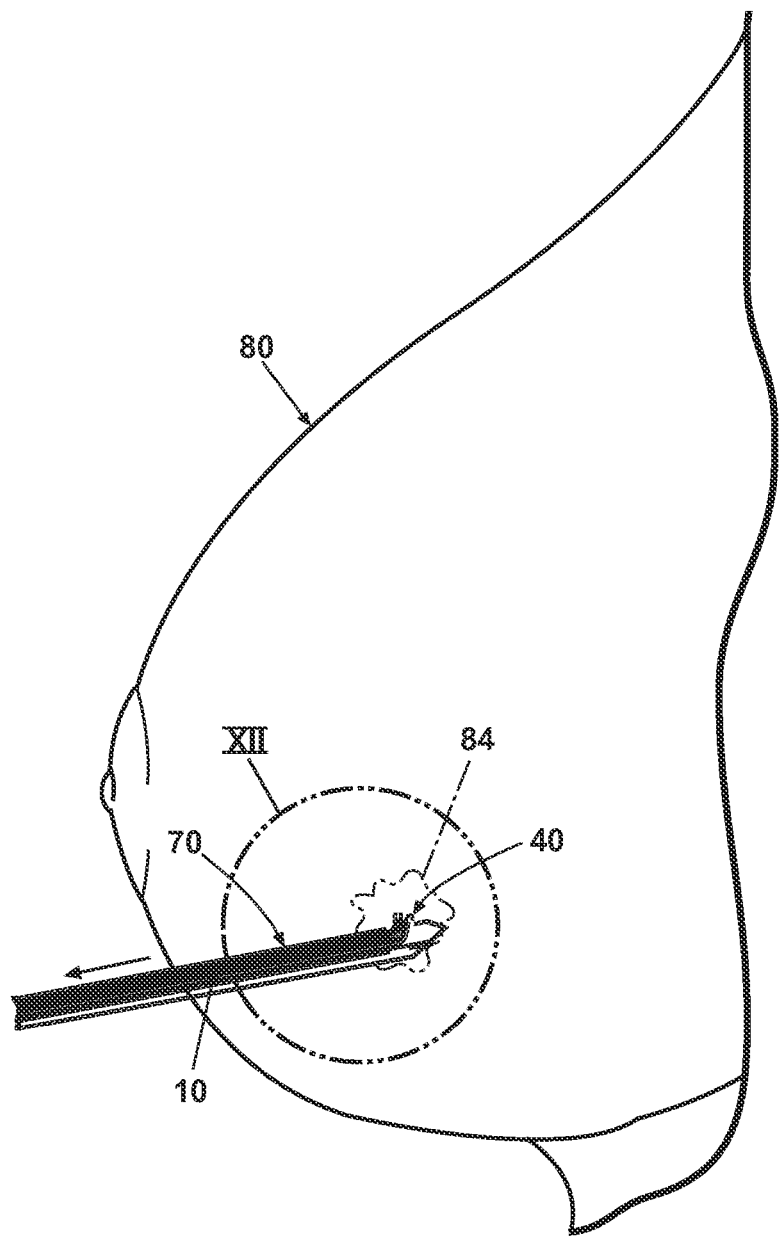
FIG. 11 is a drawing illustrating the tissue mass in an uncompressed state with the introducer system anchored in the tissue mass and the retraction of the VAB probe from the tissue mass.

The introducer system 10 is then secured in the tissue mass 80 using the anchor wire 40. Referring to FIG. 10, the anchor wire 40 is embedded at the target site 84 by moving the thread 44 through lumen 18 relative to the sheath 14 such that the anchor wire 40 emerges from tip 32. As anchor wire 40 emerges from tip 32, hook 42 expands from the straightened first configuration to the curved second configuration. As it expands into the surrounding tissue, the hook 42 pierces the adjacent tissue to imbed the anchor wire 40 at the target site 84.

After anchoring the introducer system 10, the tissue mass 80 is uncompressed by removing the compression plates 82. The VAB probe is next retracted from the tissue mass 80 as illustrated by an arrow in FIG. 11. An image is taken of the tissue mass 80 to determine if the introducer system 10 has been correctly positioned at the target site 84. Correct positioning of the introducer system constitutes a placement that allows the clip 50 to be deployed at the target site 84 and thus is determined by the position of tip 22.

Figure 12:
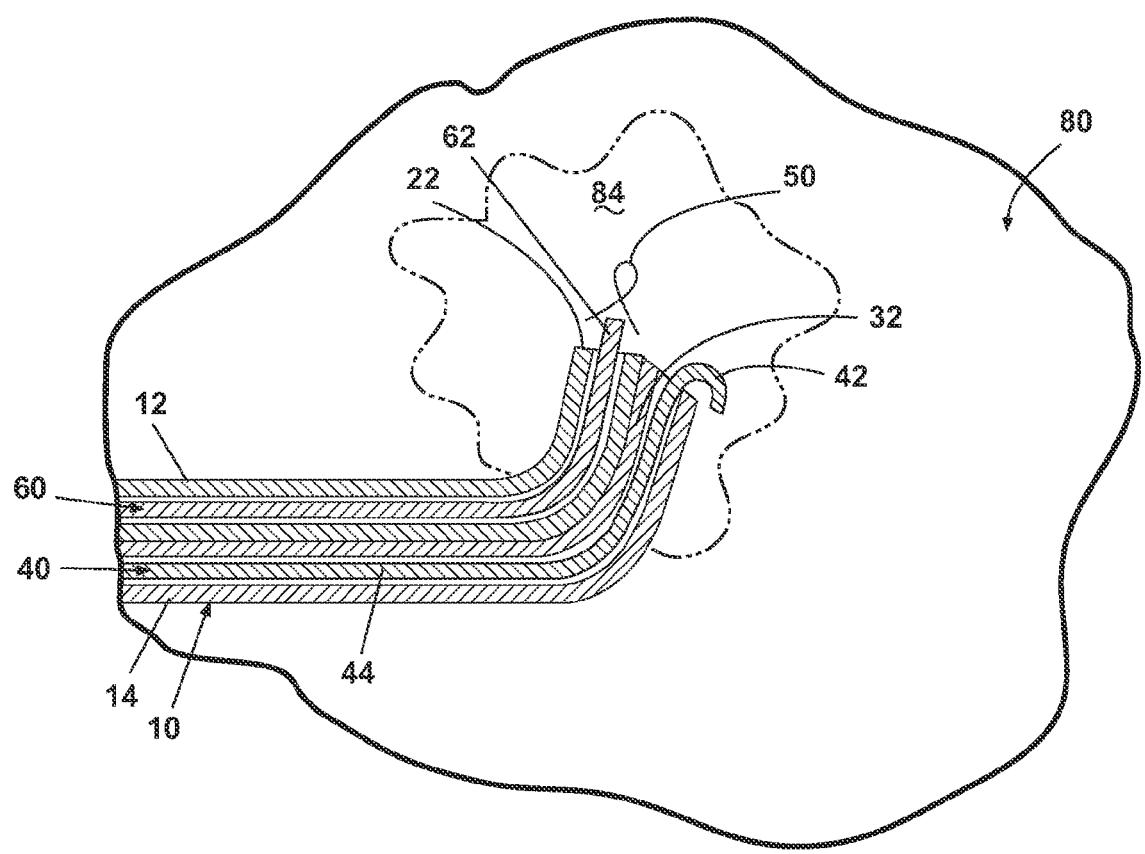
FIG. 12 is a close-up view of area XII from FIG. 11 illustrating the pushrod extended from the first lumen to push the marker clip out of the introducer system and into the tissue mass.
Figure 13:
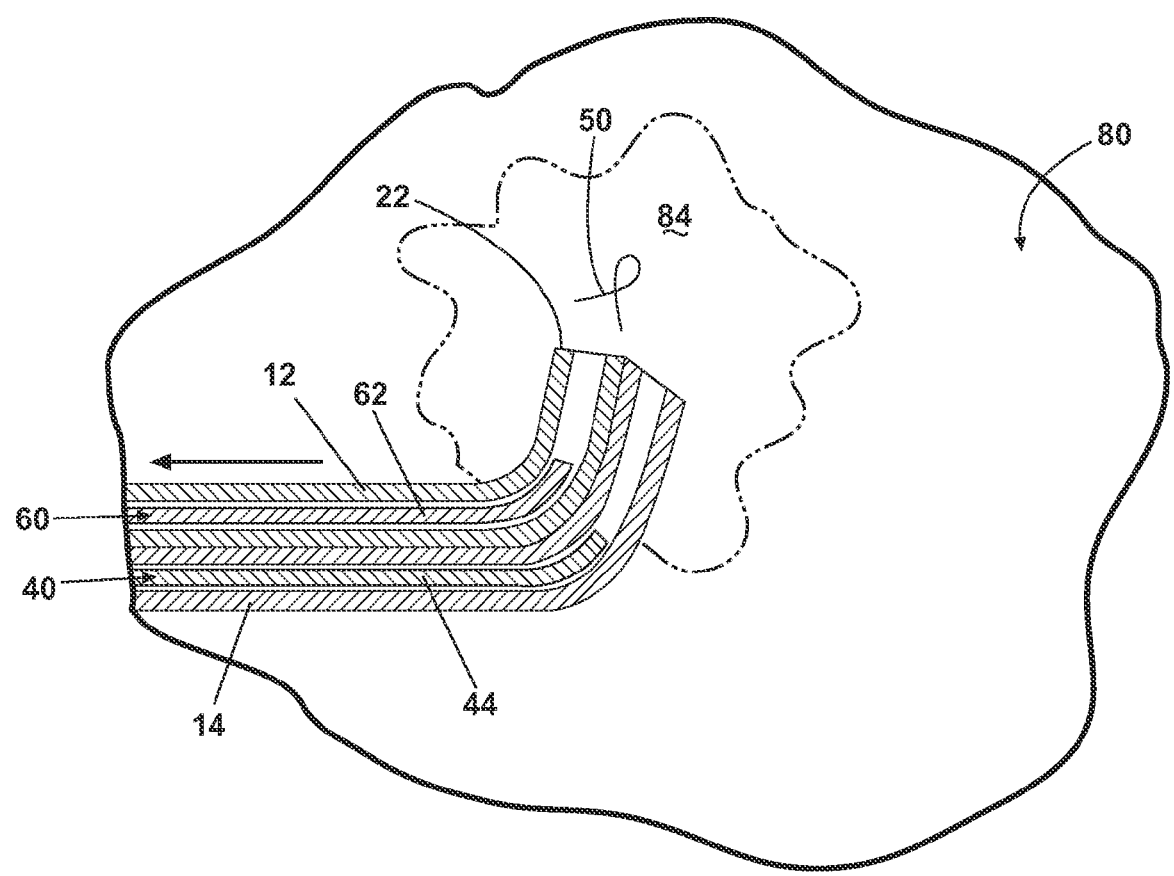
FIG. 13 is a drawing similar to FIG. 12 illustrating the marker clip implanted in the tissue mass and the retraction of the introducer system from the tissue mass.

If the introducer system 10 is correctly positioned, the clip 50 is implanted in the tissue mass 80 to mark the target site 84. Referring to FIG. 12, the pushrod 60 is moved through lumen 16 relative to the sheath 12 such that the distal end 62 pushing the clip 50 emerges from tip 22 thus deploying clip 50 at the target site 84. The pushrod 60 and the anchor wire 40 are then retracted back into their respective sheaths 12 and 14, and the introducer system 10 is retracted from the tissue mass 80, leaving the clip 50 implanted at the target site 84 as illustrated in FIG. 13.

Figure 14:
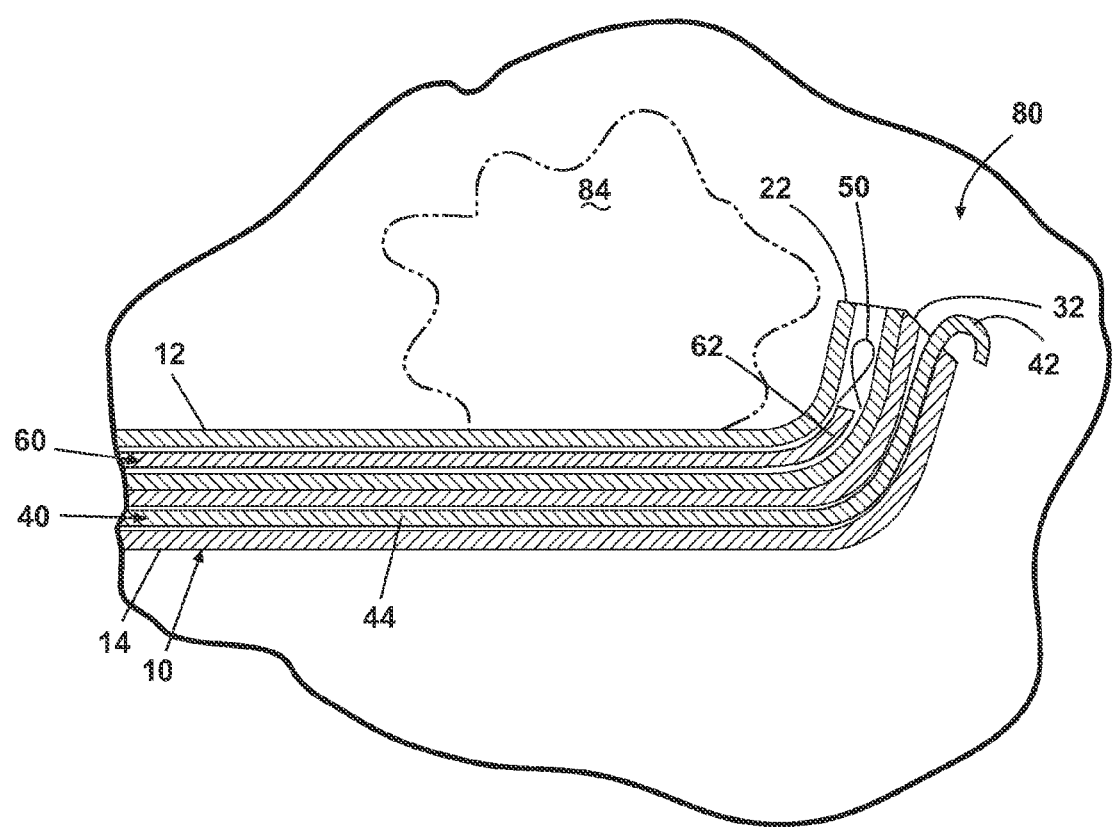
FIGS. 14-16 are schematic illustrations showing a method of relocating the introducer system within the tissue mass.
Figure 15:
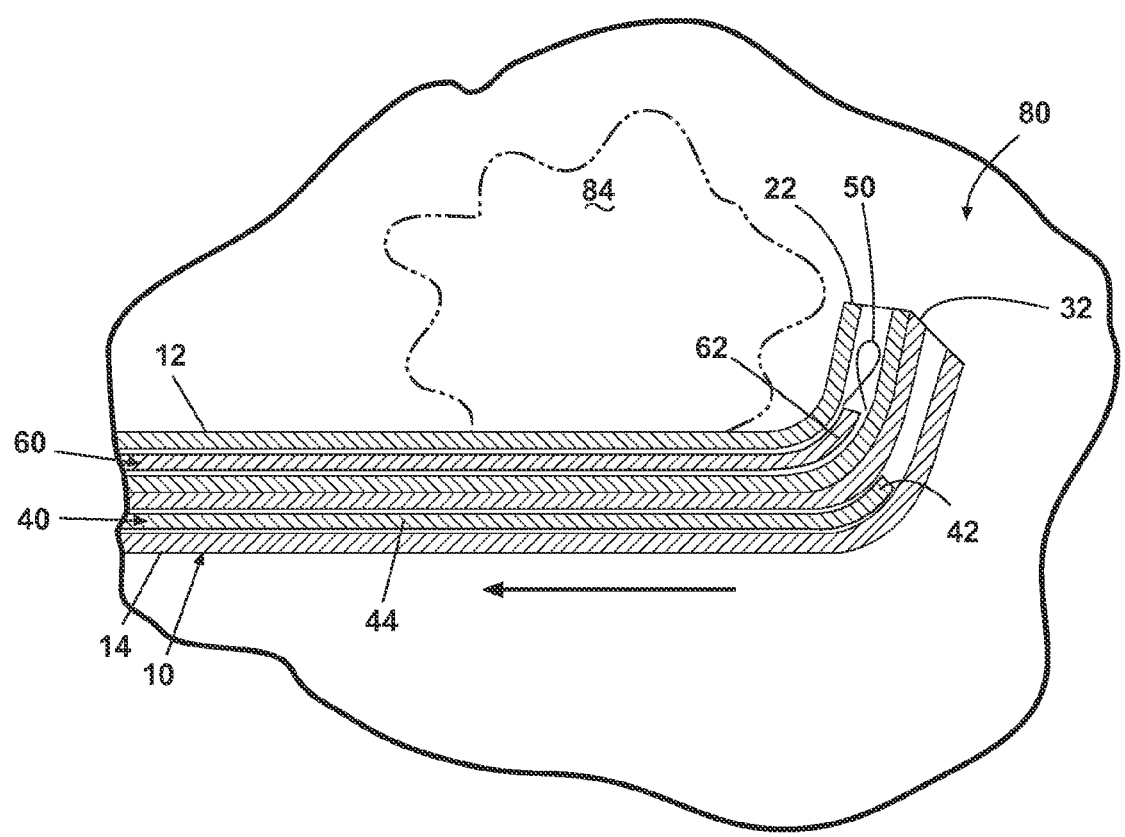
Figure 16:
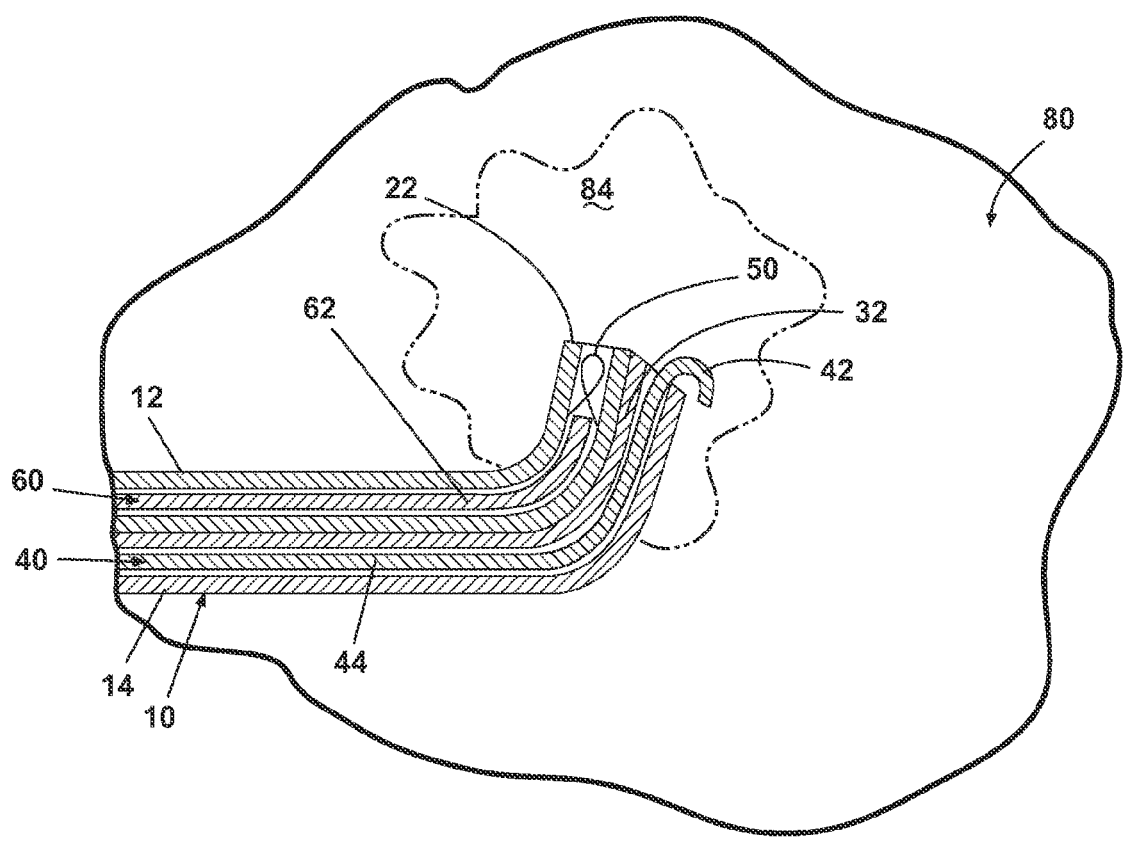

If it is determined by the image taken after the tissue mass 80 is uncompressed that the introducer system 10 has been incorrectly placed, the introducer system 10 can be repositioned within the tissue mass 80 as shown in FIGS. 14-16. Repositioning is normally accomplished with the aid of an ultrasound. In the event of misplacement, it is most often the case that the introducer system 10 is too deep or beyond the target site 84 as illustrated in FIG. 14. Referring to FIG. 15, to reposition the introducer system, the anchor wire 40 is pulled back into lumen 18 by moving the thread 44 relative to the sheath 14. The introducer system 10 is next retracted back an appropriate distance such that the tips 22, 32 are at the target site 84. The introducer system is then secured in the tissue mass 80 using the anchor wire 40 and another image can be taken to confirm that the introducer system 10 is correctly positioned at the target site 84. The introducer system 10 can be repositioned as many times as necessary until the introducer system 10 is correctly positioned as illustrated in FIG. 16. The clip 50 is then implanted in the tissue mass 80 to mark the target site 84 as previously described.

Figure 17:
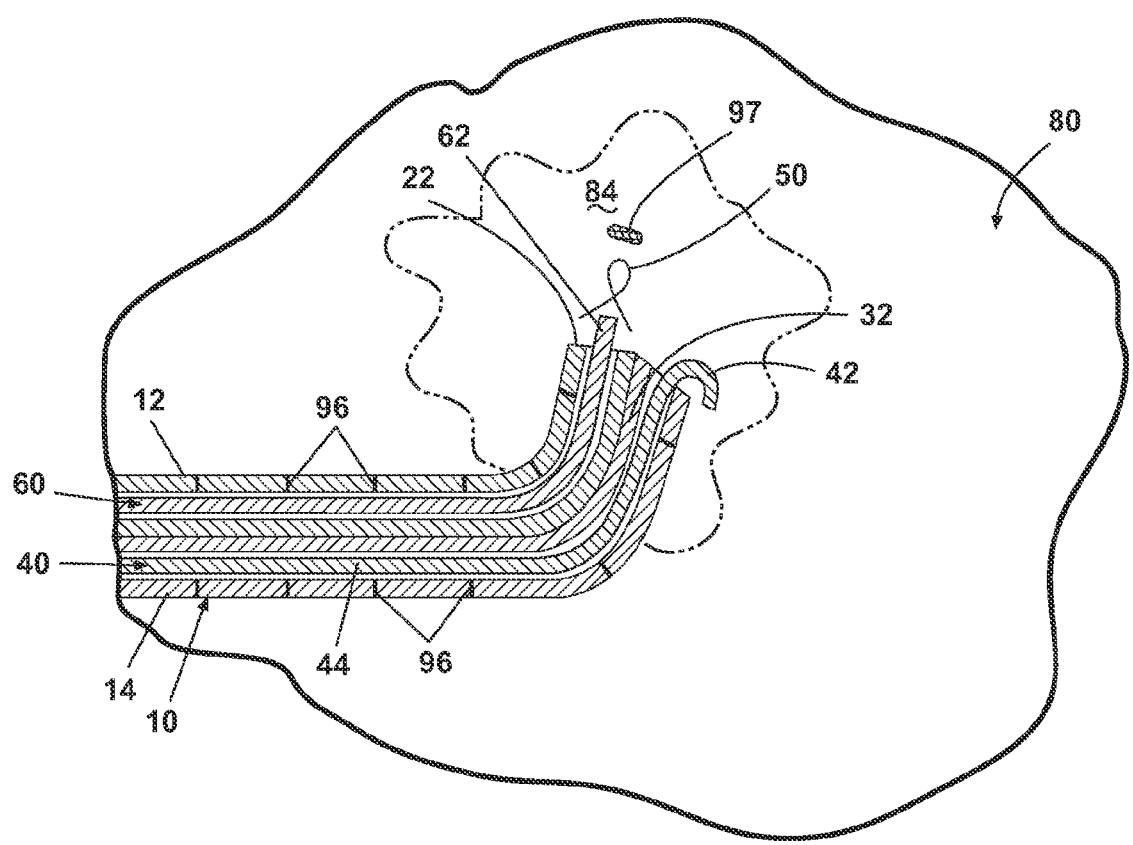
FIG. 17 is a schematic illustration of an introducer system having distance markings on the first and second lumens.

Referring to FIG. 17, to facilitate the repositioning of the introducer system 10, the sheaths 12, 14 could be provided with distance markings 96, for example centimeter markings that would enable the introducer system to be moved a distance determined from the image taken after the breast is uncompressed. Distance markings on the sheaths 12, 14 allow the introducer system 10 to be repositioned more accurately and reduces the possibility that the introducer system 10 has to be repositioned more than once to achieve correct placement of the introducer system 10.

Although a rare occurrence, the introducer system 10 can be misplaced shallow to or before the target site. To reposition the introducer system 10 in this case, a hollow cannula can be inserted over the introducer system 10 and then the cannula and introducer system 10 are advanced an appropriate distance to the target site 84. The cannula is next removed and the clip 50 is deployed.

FIG. 17 also illustrates the optional placement of a hemostatic agent 97 in addition to the placement of the clip 50. The hemostatic agent 97 can comprise a soil hemostatic agent such as a plug of collagen, chitosan, thrombin, Factor Xa, fibrinogen, nonsoluble polysaccharide, cellulose and dried gelatin; or a hemostatic agent in liquid form that is coated or impregnated in a bioabsorbable material. The hemostatic agent 97 can be loaded into the first sheath 12 along with the clip 50 and can be positioned relative to the clip 50 to be expelled prior to or just after the clip 50 as the push rod 60 is advanced. In another contemplated embodiment, the clip 50 can be coated with or encompassed by the hemostatic agent 97. The presence of the hemostatic agent 97 can prevent the clip 50 from being displaced due to bleeding at the target site 84.

While the VAB probe 70 is illustrated as the structure for providing a passageway into the tissue mass for the insertion of the introducer system, it should be noted that other insertion devices can be used and the introducer system is not limited to the VAB probe 70. For example, another insertion device can be a cannula with an axial opening or an opening in the side wall.

A second embodiment of the introducer system is shown in FIGS. 18 and 19 where like elements are identified with the same reference numerals. In this embodiment, the first sheath 12 has a partition 86 that extends the length of the sheath and divides the sheath 12 into first lumen 16 and second lumen 18. Such a configuration has a smaller cross-sectional size as illustrated in FIG. 19 and the clip 50 is deployed in the same manner as described for the first embodiment of the introducer system 10.

Figure 21:
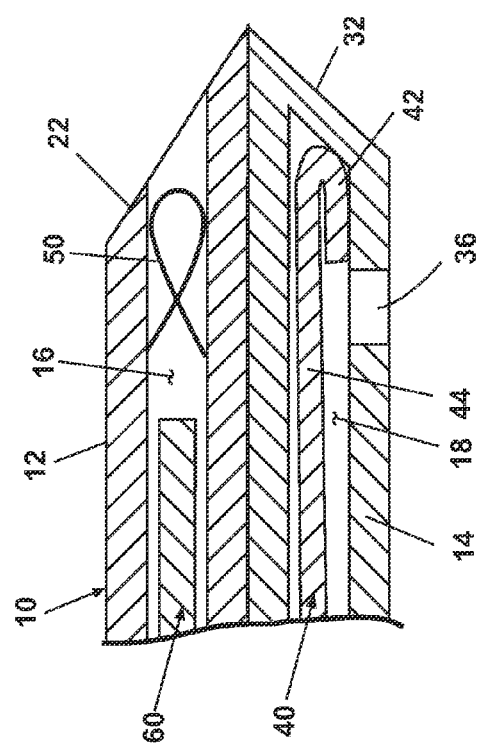
FIG. 21 is an enlarged view of the introducer system from FIG. 20 showing the anchor wire in a compressed configuration within the second lumen.
Figure 22:
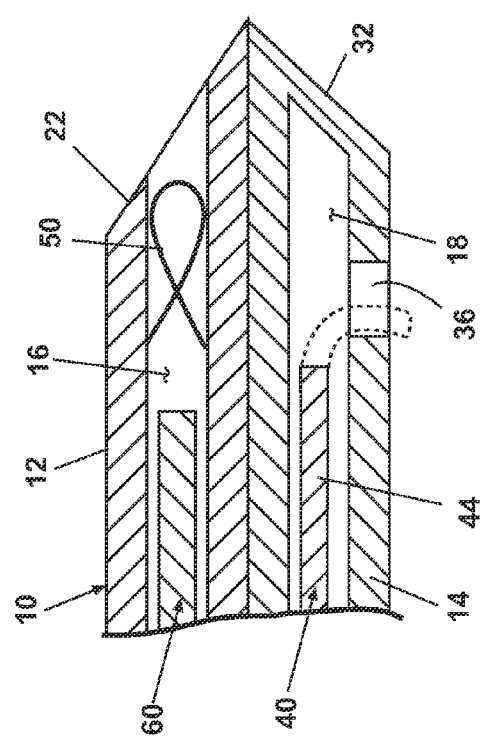
FIG. 22 is an enlarged view of the introducer system from FIG. 20 showing the anchor wire in a straight configuration within the second lumen.

A third embodiment of the introducer system is shown in FIGS. 20-22 where like elements are identified with the same reference numerals. In this embodiment, the tip 32 of the sheath 14 is closed and an opening 36 is provided in a side wall of the sheath 14, near the distal end of the sheath 14. As the anchor wire 40 is inserted into the sheath 14 it assumes the straight first configuration as shown in previous illustrations. When the hook 42 reaches the opening 36, it will assume the curved second configuration as it protrudes from the lumen 18 into the tissue mass to anchor the introducer system 10. Referring to FIG. 21, if it is then necessary to reposition the introducer system 10, the thread 44 is pushed forward, forcing the hook 42 through opening 36 and against the closed tip 32. Because of the forwardly-directed force on the wire 40, the hook 42 remains in the curved second position but is slightly compressed. After repositioning the introducer system 10, the thread 44 is pulled back, and the hook 42 exits the opening 36 to anchor the system into the tissue mass. Referring to FIG. 22, when the introducer system 10 is removed, the thread 44 is pulled back farther such that the hook 42 abuts the proximal edge of the opening 36 and assumes the straight first configuration as the hook 42 enter the second lumen 18.

A fourth embodiment of the introducer system is shown in FIG. 23 where like elements are identified with the same reference numerals. In this embodiment, both tips 22, 32 are closed and openings 26, 36 are provided near the proximal end 24, 34 of the sheaths 12, 14, respectively. A ramp 28 is provided on the distal side of the opening 26 that occludes lumen 16 and prevents advancement of the clip 50 and the pushrod 60 beyond opening 26. The ramp 28 is angled to guide the clip 50 and the pushrod 60 upward and through the opening 26.

The VAB probe 70 can be altered in a similar fashion to facilitate the movement of the introducer system 10 out of the probe 70. A second embodiment of the probe 70, shown in FIG. 24 where like elements are identified with the same reference numerals, has a ramp 88 formed on the distal side of the opening 78 such that it occludes lumen 74 and prevents the introducer system 10 from advancing beyond the opening 78. The ramp 80 is angled to guide the introducer system 10 upwards and through opening 78. While the second embodiment of probe 70 is shown in conjunction with the first embodiment of the introducer system 10, it is understood that any embodiment of the introducer system 10 can be used with the second embodiment of the probe 70.

Figure 25:
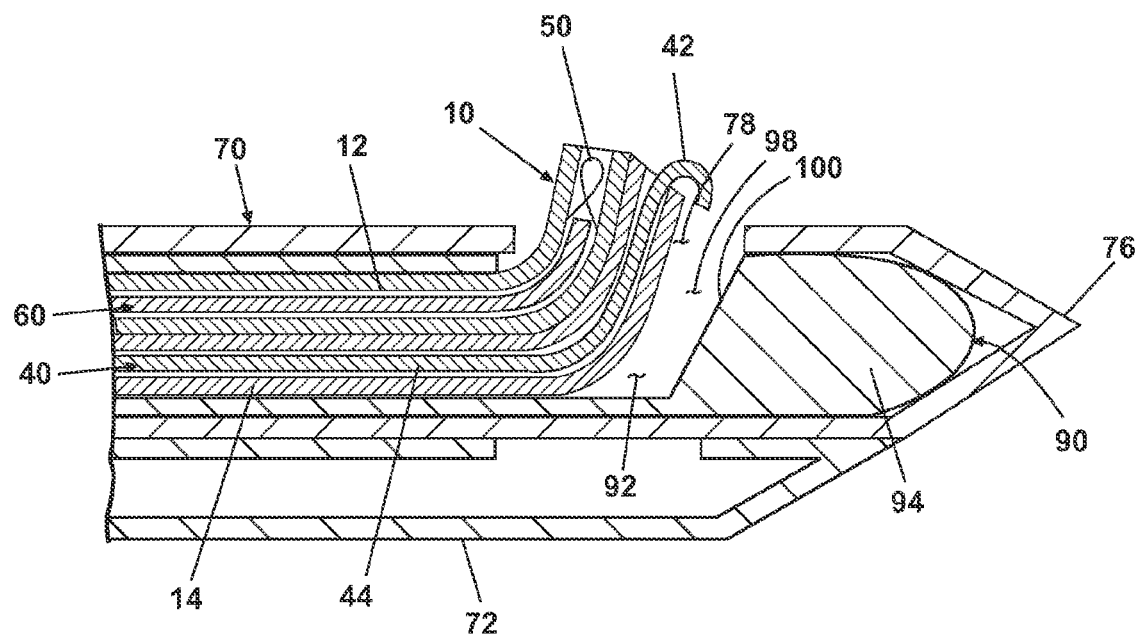
FIG. 25 is a drawing similar to FIG. 2 illustrating the introducer system contained within an outer cannula that is contained within the VAB probe.

Referring to FIG. 25, the introducer system 10 can also be inserted through an outer cannula 90 to facilitate the movement of the introducer system 10 out of the probe 70. The cannula 90 defines a lumen 92 and comprises a closed distal end 94 and a proximal end (not shown). An opening 98 near the distal end 94 is provided with a ramp 100. The opening 98 is located on the cannula 90 such that when the cannula 90 is fully inserted, the opening 98 is aligned with opening 78. The cannula 90 is considered to be fully inserted into the probe 70 when the closed end 94 contacts the closed insertion tip 76, thus aligning opening 98 with opening 78. The cannula 90 has an outer diameter sized so that is can easily fit through the lumen 74 of the probe 70 and an inner diameter sized so that the introducer system 10 can easily fit through lumen 92.

To deploy the clip 50, the outer cannula 90 is first inserted into the probe 70 and pushed forward until it is fully inserted. Full insertion of the cannula 90 can be determined when resistance is felt against the further forward movement of the cannula 90. Then, the introducer system 10 is inserted into the cannula 90 such that the introducer system 10 is guided up the ramp 100 and out of the opening 98. Next, the introducer system 10 is anchored by the anchor wire 40 and the probe 70 and cannula 90 are simultaneously retracted leaving the introducer system 10 in the tissue mass. The clip 50 is then deployed following the same steps as previously described.

While the invention has been specifically described in connection with certain specific embodiments thereof, it is to be understood that this is by way of illustration and not of limitation, and the scope of the appended claims should be construed as broadly as the prior art will permit.

The invention claimed is:

1. An apparatus for implanting a locatable marker at a target site within a tissue mass comprising:
   an insertion device including a first lumen having an exit opening; and including a first tip to facilitate insertion of the insertion device into the tissue mass to position the exit opening at the target site;
   a sheath slidably received within the first lumen and configured for deployment through the exit opening of the insertion device in to the tissue mass, the sheath including a second lumen having a distal opening;
   a locatable marker received within the second lumen and deployable through the distal opening; and
   an anchor operably coupled to the sheath and configured to extend through the exit opening of the insertion device with the sheath, the anchor being configured to move relative to the sheath to fix the location of the sheath in the tissue mass for deployment of the locatable marker at the target side.

2. The apparatus according to claim 1 wherein the insertion device is a biopsy probe.

3. The apparatus according to claim 2 wherein the probe is a vacuum-assisted biopsy probe.

4. The apparatus according to claim 1 wherein the exit opening comprises a ramp.

5. The apparatus according to claim 1 wherein the sheath comprises a third lumen having a distal opening, with the anchor received within the third lumen and deployable through the distal opening of the third lumen.

6. The apparatus according to claim 5 wherein the sheath comprises a distal terminal end, and the distal terminal end comprises an insertion tip.

7. The apparatus according to claim 6 wherein at least one of the sheath distal openings are formed in the distal terminal end of the sheath along an angled surface of the insertion tip.

8. The apparatus according to claim 1 wherein the sheath is flexible.

9. The apparatus according to claim 8 wherein the sheath comprises distance markings.

10. The apparatus according to claim 1 and further comprising a pushrod slidably received within the second lumen that deploys the locatable marker through the distal opening.

11. The apparatus according to claim 1 wherein the locatable marker is one of an imaging marker and a palpable marker.

12. The apparatus according to claim 11 wherein the locatable marker is a clip.

13. The apparatus according to claim 1 wherein the anchor comprises an anchor wire.

14. The apparatus according to claim 13 wherein the sheath comprises a third lumen having a distal opening and the anchor wire is received within the third lumen.

15. The apparatus according to claim 14 wherein the anchor wire is operable between a straight configuration where the anchor wire is contained within the third lumen and a curved configuration where the anchor wire is extended through the distal opening of the third lumen.

16. The apparatus according to claim 15 wherein the anchor wire is adapted to be embedded in the tissue mass in the curved configuration.

17. The apparatus according to claim 1 and further comprising a pair of compression plates for compressing the tissue mass prior to location of the insertion device into the tissue mass at the target site and for decompressing the tissue mass prior to implantation of the locatable marker.

18. The apparatus according to claim 1 and further comprising a hemostatic agent received within the second lumen and deployable through the distal opening.

* * * * *